United States Patent [19]

Miller et al.

[11] Patent Number: 5,380,754
[45] Date of Patent: Jan. 10, 1995

[54] TOPICAL COMPOSITION ENHANCING HEALING OF VIRAL LESIONS

[75] Inventors: Bruce W. Miller, Tierra Verde, Fla.; Richard L. Kronenthal, Fair Lawn, N.J.

[73] Assignee: ViroTex Corporation, Houston, Tex.

[21] Appl. No.: 985,279

[22] Filed: Dec. 4, 1992

Related U.S. Application Data

[63] Continuation-in-part of Ser. No. 887,101, May 19, 1992, abandoned, which is a continuation of Ser. No. 718,005, Jun. 20, 1991, abandoned, which is a continuation-in-part of Ser. No. 504,683, Apr. 4, 1990, abandoned, which is a continuation of Ser. No. 161,802, Feb. 29, 1988, abandoned.

[51] Int. Cl.$^6$ ............................................. A61K 31/21
[52] U.S. Cl. ..................................... 514/513; 514/934
[58] Field of Search ............................... 514/513, 934

[56] References Cited

U.S. PATENT DOCUMENTS

| | | | |
|---|---|---|---|
| 4,139,630 | 2/1979 | Asculai et al. | 424/283 |
| 4,462,986 | 7/1984 | Smith | 424/85 |
| 4,507,281 | 3/1985 | Asculai et al. | 424/85 |
| 4,628,063 | 12/1986 | Haines et al. | 514/626 |
| 4,874,794 | 10/1989 | Katz | 514/724 |
| 5,070,107 | 12/1991 | Katz | 514/724 |
| 5,071,879 | 12/1991 | Katz | 514/724 |

FOREIGN PATENT DOCUMENTS

| | | | |
|---|---|---|---|
| 0080032 | 6/1983 | European Pat. Off. | |
| 080879 | 6/1983 | European Pat. Off. | |
| 8503862 | 12/1985 | European Pat. Off. | A61K 31/16 |
| 0305551 | 3/1989 | European Pat. Off. | |
| 0388306 | 9/1990 | European Pat. Off. | |
| 0394928 | 10/1990 | European Pat. Off. | |

OTHER PUBLICATIONS

European Patent Application No. 86100939.7, Showa Denko K. K., published Aug. 6, 1986.

I. Tentsova, et al., "Stability of solutions of dicain in the presence of surfactants," All-Union Scientific Research Institute of Pharmacy, Moscow (Jun. 3, 1988) (English translation included).

Adriani and Zepernick, "Clinical Effectiveness of Drugs Used for Topical Anesthesia" JAMA 188(8):711–716 (May 1964).

Barry, B. W., "Mode of Action of Penetration Enhancers In Human Skin" J. Controlled Release 6:85–97 (1987).

Cassuto, Jean, "Topical Local Anaesthetics and Herpes Simplex" The Lancet 8629:100–101 (Jan. 14, 1989).

Friedman-Klein, et al., "Treatment of recurrent genital herpes with topical alpha interferon gel combined with nonoxynol 9" J. Am. Acad. Dermatol. 15(5):989–994 (Nov. 1986).

Fuchs and Levanon, "Inhibition of Adsorption of West-Nile and Herpes Simplex Viruses by Procaine" Archives of Virology 56:163–168 (1978).

Gangarosa, Louis P., "Newer Local Anesthetics and Techniques for Administration" J. Dent. Res. 60(8): 1471–1480 (Aug. 1981).

Goldberg, Charles B., "Topical Surfactant Therapy for Recurrent Herpes Simplex" The Lancet 8509:755 (Sep. 27, 1986).

Kawakatsu and Sakata, "Topical solutions containing amphoteric surfactants for prevention of viral infec- (List continued on next page.)

Primary Examiner—Marianne M. Cintins
Assistant Examiner—Russell Travers
Attorney, Agent, or Firm—Arnold, White & Durkee

[57] ABSTRACT

Multiple daily applications of a topical composition having as the active ingredients an anesthetic and a surfactant with anti-vital activity decrease the time of healing of herpes simplex viral lesions from approximately seven to ten days to five to six days, as well as decrease inflammation and pain. The composition is applied to the lesions daily, approximately every four hours, preferably beginning at the prodromal stage of infection. Relief is almost immediate, and is characterized by decreased pain, swelling, and more rapid healing as compared with the untreated lesion.

4 Claims, 2 Drawing Sheets

OTHER PUBLICATIONS tions" *Pharmacology* vol. 111, Chemical Abstracts, No. 145792s (1989).

Nicolson, Garth L., "Cell Shape Changes and Transmembrane Receptor Uncoupling Induced by Tertiary Amine Local Anesthetics" *J. Supramolecular Structure* 5:65–72 (1976).

Nicolson et al., "Effects of Local Anesthetics On Cell Morphology and Membrane-Associated Cytoskeletal Organization In Balb/3T3 Cells" *J. Cell Biology* 68:395–402 (1975).

Nixon et al., "Interspecies Comparisons of Skin Irritancy" *Toxicology and Applied Pharmacology* 31:481–490 (1975).

Poste et al., "Local anesthetics affect transmembrane cytoskeletal control of mobility and distribution of cell surface receptors" *Proc. Nat. Acad. Sci. U.S.A.* 72(11):4430–4434 (Nov. 1975).

Reichman, et al., "Treatment of Recurrent Genital Herpes Simplex Infections With Oral Acyclovir A Controlled Trial" *JAMA* 251(16) 2103–2107 (Apr. 27, 1984).

Shimakage, et al., "Local injection of human fibroblast interferon-$\beta$ effective in malignant skin tumors" *Skin Res.* 24(5):732–741 (1982) (Biol. Abst. 76 (11):8998, No. 81880).

Svobodova, et al., "Long-term cultivation of cells derived from guinea pig tongue" *Acta Virol. (Prague)* 21(4):349 (1977) (Biol. Abst. 66(1):596, No. 6159 (1978)).

Vontver, et al., "Clinical course and diagnosis of genital herpes simplex virus infection and evaluation of topical surfactant therapy" *Am. J. Obstet. Gynecol.* 133(5):548–554 (1979).

Sarpotdar et al., "Evaluation of penetration enhancement of lidocaine by nonionic surfactants through hairless mouse skin in vitro" *Journal of Pharmaceutical Sciences* 75(2):176–181 (Feb. 2, 1986).

"Evaluation of Topical Antiviral Therapy In A Primary Genital Herpes Simplex Virus Type 2 (HSV-2) Infection of Guinea Pigs" Final Report by Earl R. Kern, Ph.D., Department of Pediatrics, University of Alabama at Birmingham, Birmingham, Ala., May 16, 1990.

Poste and Reeve, "Inhibition of virus-induced cell fusion by local anesthetics and phenothiazine tranquilizers," *J. Gen. Virol.* 16:21–28 (1972).

Wunderlich and Sydow, "Lytic action of neurotropic drugs on retroviruses in vitro," *Eur. J. Cancer*, 16:1127–32 (1980).

Miller and Lenard, "Antihistaminics, local anesthetics, and other amines as antiviral agents," *Proc. Natl. Acad. Sci. U.S.A.* 6:3605–3609 (1981).

Merchant et al., "Unsaturated and free fatty acid inhibition of herpes simplex virus," *Microbios Letters* 35:71–78 (1987).

L. R. Stanberry, E. R. Kern, J. R. Richards, T. M. Abbott, and J. C. Overall Jr., "Genital Herpes in Guinea Pigs: Pathogenesis of the Primary Infection and Description of Recurrent Disease" *J. Infect. Dis.*, 146:397–404 (1982).

W. R. Hubler, Jr., T. D. Felber, D. Troll, and M. Jarratt, "Guinea Pig Model for Cutaneous Herpes Simplex Virus Infection" *J. Invest. Dermatol.*, 62:92–95 (1974).

M. Lieberman, T. W. Schaefer, and P. E. Came, "Chemotherapy of Cutaneous Herpes Virus Infection of Hairless Mice" *J. Invest. Derm.*, 60:203–206 (1973).

J. Descamps, E. DeClercq, P. J. Barr, A. S. Jones, R. T. Walker, P. F. Torrence, and D. Shugar, "Relative Potencies of Different Anti-Herpes Agents in the Topical Treatment of Cutaneous Herpes Simples Virus Infection of Athymic Nude Mice" *Antimicrob. Agents Chemother.*, 16:680–682 (1979).

T. J. Hill, H. J. Field, W. A. Blyth, "Acute and Recurrent Infection with Herpes Simplex Virus in the Mouse: a Model for Studying Latency and Recurrent Disease" *J. Gen. Virol.*, 28:341–353 (1975).

Poste et al. 70 CA: 147965s 1972.
Wunderlech et al. 93 CA:230706j 1980.
Miller et al. 95 CA: 90885p 1981.
Vickonova et al. 79 CA:38916x 1973.
Asculai et al. 85 CA:83237m 1976.
Asculai et al. 86 CA:195230f 1977.
Merchant et al. 108 CA 15820q 1988.
Merck Index 10th Ed #'s 1020, 3840, 5977, 7659, 8421, 8474, 8654, 9014.

TOPICAL COMPOSITION ENHANCING HEALING OF VIRAL LESIONS

This is a continuation-in-part of U.S. Ser. No. 07/887,101, filed May 19, 1992, now abandoned, which is a continuation of U.S. Ser. No. 07/718,005, filed Jun. 20, 1991, now abandoned, which is a continuation-in-part of U.S. Ser. No. 07/504,683, filed Apr. 4, 1990, now abandoned, which is a continuation of U.S. Ser. No. 07/161,802, filed Feb. 29, 1988, now abandoned.

BACKGROUND OF THE INVENTION

Herpes simplex virus (HSV) causes infections characterized by inflammation of skin and mucosal membranes of the mouth and genital areas. The type of HSV most commonly associated with lesions of the mouth and facial region is Type 1 HSV. Type 2 HSV is most commonly associated with lesions of the genital region.

The symptoms of HSV generally include erythema, inflammation, pain, and lesions. Symptoms initially include tingling, pain, and/or swelling at the site of infection, followed by lesion formation (papules and vesicles) with scar formation and healing occuring in approximately ten to fourteen days. After the initial infection, recurrent attacks may occur throughout life in response to various stimuli, including changes in body temperature, stress, ultraviolet radiation and exposure to chemicals.

Treatments for HSV infections are limited in efficacy. There is no known cure at this time, although various anti-viral compositions are being marketed with claims of beneficial effects. Most anti-viral compounds currently in use are synthetic nucleoside analogs which interfere with the replication of viral DNA or RNA. The mode of action of these compounds is to directly interfere with the action of DNA or RNA polymerase or chain termination after incorporation into specific nucleic acid polymers.

Many synthetic nucleoside analogs have been tested for the ability to inhibit viral replication. However, most of these have unacceptable toxicity and cannot be used for treating humans. Interestingly, many useful nucleoside analogs have principal activity against the herpes group of viruses which include varicella-zoster virus, herpes simplex virus, Epstein Barr virus and cytomegalovirus.

Currently, there is only one commercially available FDA approved nucleoside analog which has been shown to be efficacious in the treatment of lesions of the skin produced by herpes simplex virus. This compound is produced by Burroughs Wellcome Company and has been given the name Acyclovir. Acyclovir has been shown to be effective in the treatment of primary genital herpes and, in many individuals, can reduce or prevent prevent recurrences when taken on a daily basis over long periods of time. Acyclovir (acycloguanosine) is administered systemically for treatment of HSV with some success. Topical acyclovir has been found to be somewhat effective for the primary lesion but not for recurrent lesions. There is a wealth of clinical and scientific literature relating to the use of acyclovir in herpes infection.

Interferon has also been tested systemically and topically against HSV but with only limited efficacy. There are so many side effects associated with systemic administration of anti-virals that topical treatments are greatly preferred. Unfortunately, the topical administration even of the compounds having some efficacy when administered systemically is generally ineffective.

It is therefore an object of the present invention to provide topical compositions and methods of use thereof for the alleviation of the symptoms associated with herpes simplex infections or other viral lesions.

It is a further object of the present invention to provide topical compositions for alleviation of the symptoms of HSV infection with minimal side effects and relief from inflammation and pain normally associated with vital lesions.

SUMMARY OF THE INVENTION

The present invention provides a topical composition for reducing the symptoms of viral lesions or shortening time of healing. The composition comprises a therapeutically effective amount of the combination of an anesthetic, a surfactant and a topical carrier. Varying amounts of anesthetic and surfactant may be used to achieve efficacious results, e.g., for anesthetic concentrations of from about 0.05% to 25% by weight, 0.25% to 10% by weight, and most preferably 1 to 5% by weight, and for surfactant, concentrations of from about 0.05 to 50% by weight, 1 to 10% by weight, and 0.5 to 5% by weight.

In preferred embodiments, the anesthetic is selected from the group consisting of esters, amides, ethers, and combinations thereof and, in particular, topical anesthetics and other anesthetics which may be formulated in accordance with the invention and applied topically, including procaine, chloroprocaine, tetracaine, propoxycaine, benzocaine, cocaine, proparacaine, bupivacaine, dibucaine, etidocaine, lidocaine, mepivacaine, prilocaine, dyclonine, pramoxine and combinations thereof.

The surfactant is selected from the group consisting of anionic, nonionic, and cationic surfactants and combinations thereof. Suitable ionic surfactants include anionic surfactants such as monovalent salts, e.g., sodium and potassium salts of alkyl, aryl and alkyl-aryl sulfates and sulfonates, particularly those with from about 8 to about 22 carbon atoms, and cationic surfactants, such as quaternary ammonium salts. Suitable nonionic surfactants include polyethylene oxide adducts of fatty alcohols, e.g., alkylated polyoxyethylenes, alkylated polyoxyethylene-polyoxypropylene copolymers, and the surfactant nonoxynol.

The surfactant and the anesthetic are formulated together in a pharmaceutically acceptable topical carrier, which may take any of a number of acceptable forms. Suitable carriers include aqueous carriers and oleaginous carriers. The composition may contain one or more additional agents, including antimicrobial agents, anti-viral agents, anti-fungal agents, buffering agents, antioxidants, preservatives, coloring agents, fragrances, lubricants, moisturizers, sunscreens, drying agents and the like and, more specifically, may include ingredients such as stearic acid, lauramide DEA, borax, eucalyptus oil, beeswax, preservative and methylparaben.

Optimally, the composition will be effective to reduce the viral titer of lesions resulting from a viral disease and, in particular, herpetic lesions. The invention also includes methods for reducing the symptoms of viral lesions or decreasing time of healing by topically administering compositions of the invention to a lesion or affected area, preferably at least about once every twelve hours and, more preferably, about every four hours. The composition is applied to the lesions daily, preferably beginning at the preliminary or prodromal stage of infection. Relief is almost immediate, and is characterized by decreased pain, swelling, and more rapid healing as compared with the untreated lesion.

DETAILED DESCRIPTION OF THE INVENTION

The formulation for alleviation of the symptoms of HSV lesions has two essential components, a topical or local anesthetic and a surfactant, which are added to a conventional carrier cream, ointment, solution or gel containing appropriate stabilizers, buffers and preservatives for topical application to the lesion.

Topical anesthetics conveniently can be classified as esters, ethers or amides and include the following anesthetics which may be useful for the practice of the invention:

| Esters | Amides | Ethers |
|---|---|---|
| Tetracaine | Dibucaine | Dyclonine |
| Benzocaine | Lidocaine | Pramoxine |
| Proparacaine | | |
| Procaine | | |
| Cocaine (not a legal drug in the United States) | | |
| Butambin picrate (trinitrophenol 2-butyl-p-aminobenzoate) | | |
| Propoxycaine | | |

There are other anesthetics used for injection, e.g., spinal anesthesia, which are not usually listed as topicals but are expected to work well on lesions where intact skin does not present a barrier.

Some examples are:
Chloroprocaine
Bupivacaine
Etidocaine
Mepivacaine
Prilocaine

The preferred anesthetic is tetracaine (either as the hydrochloride or other salt or as the free base). Tetracaine is the preferred anesthetic because it is the anesthetic first tested and demonstrated to penetrate skin effectively, it has in vitro viral anti-replication activity, and it is on the FDA monograph list which allows marketing as an over-the-counter (OTC) product for fever blisters and cold sores at concentrations up to 2% by weight.

In the preferred embodiment, the anesthetic is combined with a carrier in a concentration range of between 1 and 2% by weight; however, the anesthetic may be present in varying concentrations, for example, between approximately 0.05 and 25%, by weight, between approximately 0.25 and 10% by weight, between approximately 0.5 and 10% by weight, and between approximately 1 and 5% by weight. Of course, the exact dose of anesthetic to be employed in a given formulation will depend on a number of factors such as the particular anesthetic to be employed. For example, in compositions containing benzocaine as the anesthetic, an exemplary preferred dose range is between approximately 1 and 20% by weight, in compositions containing lidocaine, an exemplary preferred dose range is between approximately 1 and 20% by weight and in compositions containing tetracaine an exemplary preferred dose is approximately 0.5%.

In addition to the local anesthetic, the compositions of the invention will also contain a therapeutically effective amount of a surfactant. Surfactants have been discovered to have potent virucidal activity in vitro with a very low degree of toxicity. It is believed that the surfactant may both physically inactivate viruses and may facilitate penetration of the anesthetic to the deeper, infected layers of the skin, enhancing the effectiveness of the individual compounds to facilitate healing.

In a preferred embodiment, the surfactant in the formulation is sodium lauryl (or dodecyl) sulfate, also referred to as "SLS", a common surfactant found in toothpaste and other cosmetic preparations, known to "unfold" the tertiary structure of proteins but not previously known to have actual virucidal activity. Sodium lauryl sulfate is an anionic surfactant with a negatively charged sulfate group. Sodium lauryl sulfate is also capable of penetrating intact skin very effectively. Other monovalent sulfur-containing surfactants, e.g., the sodium or potassium alkyl, alkyl-aryl, and aryl sulfates or sulfonates can be used in accordance with the invention.

In addition, cationic surfactants may be active, alone or in combination with SLS. An example is trimethyldodecylammonium chloride, a positively charged quaternary ammonium complex which has antimicrobial characteristics. Other quaternary salts, with and without long chain moieties to provide surface activity, may also be useful.

Nonionic surfactants, the most common being nonoxynol, may also be useful. Common nonionic surfactants include nonoxynol, polyoxyethylenes, polyoxyethylene-polyoxypropylene copolymers and alkyl sorbitols.

In the preferred embodiment, the surfactant is combined with carrier in a concentration range of between approximately 0.5 to 2%, by weight; however, the surfactant may be present in a concentration of between approximately 0.1 to 10%, by weight. The selected surfactants may also be combined in varying concentration ranges, for example, between approximately 0.1 to 20% by weight, between approximately 0.05 to 50% by weight, between approximately 1.0 and 10% by weight, and between approximately 0.5 and 5.0% by weight.

The composition can also contain antimicrobials, including antibiotics, antifungals, and other anti-viral compounds, which may complement or supplement the activity of the basic composition. Suitable antibiotics include tetracycline, polymyxin B or other common antibiotics used in topical compositions, especially over-the-counter formulations. Examples of useful antifungals include tolnaftate and micatin. Examples of antivirals include interferon, either natural or recombinant, as well as nucleoside analogs, e.g., Acyclovir. Counter-irritants such as camphor and menthol, drying agents such as benzyl alcohol, resorcinol and phenol, and astringents such as zinc sulfate and tannic acid can also be added to the composition as can other types of agents such as sunscreens, emollients, preservatives, fragrances, antioxidants, color additives, lubricants, moisturizers or drying agents. For example, a sunscreen, e.g., PABA, can be added to the formula since it is known that cold sores can be triggered by ultraviolet radiation.

The composition can be prepared in almost any relatively inert topical carrier. Generally, the formulation could take several forms, e.g., cream, gel, ointment, "Chapstick" and solution forms. Each of these formulations may contain the two active ingredients as well as microorganism growth inhibitors (preservatives). Many such carriers are routinely used and can be obtained by reference to pharmaceutical texts. Examples include polyethylene glycols (PEG), polypropylene copolymers (Pluronics), and some water soluble gels.

The preferred carrier is an emulsified cream, but other common carriers such as certain petrolatum or mineral oil-based ointments in which the surfactant and anesthetic are dispersible can be substituted. For example, one suitable cream formulation used in animal studies and clinical experiments is described below:

| COMPONENT | PERCENT (approximate) |
|---|---|
| Deionized water | 69 |
| Stearic Acid | 22 |
| Sodium lauryl sulfate | 1 |
| Beeswax | 1 |
| Tetracaine | 2 |
| Borax | 0.4 |
| Lauramide DEA | 3.6 |
| Methylparaben | 0.3 |
| Eucalyptus Oil | 0.03 |

At this time, the preferred composition of the composition most effective in enhancing healing of viral lesions is: (all percents are by weight):
  methylparaben, 0.25% (0.25 to 0.5%)
  borax, 0.5% (0.3 to 0.6%)
  lauramide DEA, 4% (0.3 to 0.4%)
  stearic acid, 20% (15 to 25%)
  beeswax, 0.8% (0.5 to 1.5%)
  tetracaine, 1.8% (1 to 2%)
  sodium lauryl sulfate, 0.8% (0.1 to 3%)
  eucalyptus oil 0.025% (0.01 to 0.0.5%)
  PCMX 0.4% (0.3 to 0.5%)
  water to a total of 100%

Gels, i.e., thickened aqueous or alcoholic solutions, containing the active ingredients and stabilizers may be clear and/or colored with suitable dyes. Suitable thickeners may include carboxymethylcellulose, polyvinylpyrrolidone or polyacrylic acid salts.

Hydrophilic or hydrophobic ointments may be employed as carriers. However, hydrophobic ointments, such as Vaseline, which are based upon hydrocarbon and wax derivatives may not be as efficacious as the hydrophilic ointments because they may impede penetration into the skin. Hydrophilic ointments such as those based upon propylene glycol, polyalkylene glycols, and the Pluronics are therefore preferred for ointment formulations. Propylene glycol, as a base, is preferable to polyethylene glycol.

"Chapstick" formulations may be employed in situations, e.g., for treatment of cold sores, where ease of application is a primary objective.

Solutions, i.e., dilute aqueous preparations containing active ingredients and preservatives but without substantial concentrations of thickeners, can be sprayed upon the affected surface with an aerosol pump. This type of delivery may be of value for treating larger areas of painfully sensitive skin in indications such as shingles.

In most cases, it is preferred that the pH of the carrier containing the active ingredients is adjusted to a pH of about 6 to 7, using, as buffering agents, ingredients such as borax although other acceptable buffering agents could be used.

Additional additives may include antioxidants, fragrance, color, water, preservatives (either antioxidants or antimicrobials), lubricants, moisturizers, or drying agents.

The composition is applied by the patient to the lesions one to six times daily, most preferably beginning immediately after the prodrome is sensed. Enough composition is applied to cover the lesion or the prodromal area.

The formulation has been demonstrated to be active against both HSV 1 (cold sores and fever blisters) and HSV 2 (genital herpes). However, it may be active against other viruses including herpes zoster (causing shingles) and the varicella virus causing chicken-pox, which are similar in structure or mechanism of infection.

The invention will be further understood by reference to the following examples:

EXAMPLE 1

Determination of the ability of selected components of the composition to directly inactivate or inhibit the replication of herpes simplex virus type-2.

Cells

A continuous line of human embryo lung cells (MRC-5) were grown in Eagle's minimal essential medium (MEM) in Earle's salts supplemented with 2 mM L-glutamine, 10 mg/ml gentamicin, 0.25 mg/ml amphotericin B (Fungisone) and 10% heat-inactivated fetal calf serum (growth medium). Cells were grown at 37° C. in a humidified 5% $CO_2$ atmosphere or in closed flasks. Maintenance medium was the same basic composition, except the concentration of fetal calf serum was 2%. Vero cells (continuous line of green monkey kidney cells) were grown in the same manner as MRC-5 cells.

Viruses

A clinical isolate from a genital lesion of herpes simplex virus, Type 2 (HSV-2), was used.

Stocks of viruses were grown by infecting MRC-5 cells at a multiplicity of 0.01 plaque forming units (PFU) per cell and harvested in maintenance medium. Virus was harvested by three cycles of freezing at $-70°$ C. and thawing, followed by centrifugation at $1000 \times g$ at 4° C. for 15 minutes to remove cell debris. Resulting virus stocks were aliquoted and frozen at $-70°$ C.

Chemicals

Stock solutions of procaine hydrochloride, niacin, sodium lauryl sulfate, and tetracaine were prepared from commercially available reagents. Stock solutions were prepared in Eagle's MEM without supplements and stored at 4° C.

Cytotoxicity Studies

Cytotoxicity assays were performed in MRC-5 cells and in Vero cells. The test compound was dissolved in maintenance medium at selected concentrations and inoculated onto MRC-5 or Vero cells in 96 well tissue culture plates. Each concentration was inoculated in triplicate. The plates were incubated at 37° C. in 5% $CO_2$ and graded for cytotoxicity at 24, 48 and 72 hours after inoculation. The highest concentration of compound showing 50% cytotoxicity after 72 hours was designated the end point.

These studies yielded the following results. Procaine HCl exhibited significant cytotoxicity in MRC-5 cells at concentrations above 0.25% after 24 hr incubation. Procaine HCl was not as cytotoxic in Vero cells as it was in MRC-5 cells, showing significant toxicity only at concentrations above 2.0%. Tetracaine HCL was also more toxic to MRC-5 cells, showing significant toxicity at concentrations above 0.03% at 24 hr, but not in Vero cells. Niacin was non-toxic in MRC-5 cells up to concentrations of 0.25%. Sodium lauryl sulfate was highly toxic to MRC-5 cells at concentrations above 0.0025%.

Inactivation Studies

To determine if a test compound directly inactivates HSV-2, 0.5 ml of serial dilutions of the compound to be tested was mixed with 0.5 ml of stock HSV-2 (titer=$5.0\times10$ PFU/ml) and incubated at room temperature for 30 minutes. After 30 minutes, the compound-virus mixture was diluted 10,000 fold in maintenance medium and virus recovery was determined by inoculating MRC-5 cells. The cells were graded for cytopathic effect after 24 hr, 48 hr, and 72 hr.

These studies yielded the following results. Procaine HCl did not directly inactivate HSV-2 at the concentrations tested, up to 4%. Tetracaine HCl did not directly inactivate HSV-2 at the concentrations tested, up to 2%. Niacin did not directly inactivate HSV-2 at the concentrations tested, up to 0.25%. Sodium lauryl sulfate directly inactivated HSV-2 at concentrations ranging from 30% down to 0.02% and partially inactivated the virus at concentrations down to 0.0025%. No inactivation occurred at a concentration of 0.00032%.

Anti-viral Studies

Anti-viral activity, i.e., the ability of a compound to inhibit replication of virus in cells, was measured by infecting confluent monolayers of MRC-5 cells in $12\times100$ mm culture tubes at a multiplicity of infection (MOI) of 3.0 plaque forming units (PFU) per cell of HSV-2 by removing the maintenance medium, washing the monolayers three times with phosphate buffered saline (PBS), and adding 0.1 ml of HSV-1 suspended in PBS. The multiplicity of infection was calculated by counting the number of viable cells in a duplicate tube and diluting the stock virus to produce a viral inoculum in a volume of 0.1 ml which contained three times the PFUs as the number of cells counted. After a 60 minute absorption period, the inoculum was removed and 4 mls of test compound at appropriate concentrations in maintenance medium or maintenance medium (control) was added.

The tubes were incubated at 37° C. for an additional 23 hours. At 24 hours post-infection, the medium was removed and the monolayers were washed twice with PBS and frozen and thawed 3 times in 1 ml of maintenance medium. Virus yields were determined by serial end-point titrations in 96-well tissue culture plates containing MRC-5 cells. All experiments were tested in triplicate, 50% end-points were calculated and titers were expressed in TCID 50 units. Anti-viral effect was determined by subtracting the difference between the TCID 50s of the test compound and from the TCID 50s of HSV-2 virus stock titrated in the same experiment and calculated in percentages.

These studies yielded the following results. Concentrations of procaine HCl up to 2% were unable to inhibit the replication of HSV-2. Tetracaine HCl partially inhibited 90% of the replication of HSV-2 at 0.25% and 0.5%. It is likely that higher concentrations of tetracaine HCl would completely inhibit the replication of HSV-2. Niacin did not inhibit the replication of HSV-2. Sodium lauryl sulfate did not inhibit viral replication at concentrations of 0.0025% and 0.0013%.

In summary, the results show that SLS is the most active ingredient of those tested as an inactivator of HSV-2 at concentrations ranging down to 0.02%, and that tetracaine HCl has significant anti-viral activity at a concentration of 0.5%, although procaine HCl does not. At high concentrations, sodium lauryl sulfate may also act by desquamation of infected cells in the lesions, causing their rapid removal and enhanced healing as a result.

EXAMPLE 2

Evaluation of the in vivo efficacy of selected components of the composition on a primary genital herpes simplex virus Type 2 infection of guinea pigs.

The anti-viral activity of several compounds in a primary genital HSV-2 infection of guinea pigs was tested. The experiments were placebo-controlled and uninfected animals were treated with each of the preparations to assess skin irritation. Groups treated with 5% Acyclovir were included as positive controls.

Materials and Methods

Genital HSV-2 Infection of Guinea Pigs

The MS strain of HSV-2 was utilized to infect animals. Female Hartley strain guinea pigs, Charles River Breeding Laboratories, Kingston, N.Y., weighing 250 to 300 g were inoculated intravaginally with $1.4\times10^5$ plaque forming units of HSV-2 one hour after being swabbed for the removal of vaginal secretions.

Treatment of Guinea Pigs

Groups of ten infected guinea pigs were treated topically, 0.1 ml intravaginally and 0.1 ml on external genital skin, three times daily, approximately every eight hours, for seven days, beginning either 6 hr or 48 hr after HSV inoculation. Groups of three uninfected animals were used to assess toxicity of each preparation.

Sample Collection and Virus Assays

To determine the effect of treatment on vaginal virus replication, swabs of vaginal secretions were obtained on days 1, 3, 5, 7 and 10 after HSV-2 inoculation, placed in a tube containing 2.0 ml of media, vortexed and frozen at $-70°$ C. until titrated for HSV-2. When all samples were collected, they were thawed, diluted serially and HSV-2 titers determined using a microtiter CPE assay in rabbit kidney cells. Mean peak virus titers and areas under the virus titer-day curves were calculated and analyzed.

Scoring of External Genital Lesions

To determine the effect of therapy on the development and spread of external genital lesions, lesion severity was scored on a 0–5+ scale through the primary infection (21 days). Mean peak lesion scores and the area under the lesion score-day curves were calculated and analyzed.

Evaluation of Efficacy

The number of animals infected over the number inoculated, lesion score-day areas and virus titer-day areas under the curve, peak lesion scores and peak virus titers between untreated and placebo-treated or placebo-treated and drug-treated animals were compared using the Mann-Whitney U rank sum test. A p-value of 0.05 or less was considered significant.

| Samples: | |
|---|---|
| 1A | base formulation without procaine with SLS |
| 2A | base formulation without procaine or SLS |
| 3A | base formulation without SLS, with 1.8% procaine |
| 3 | base formulation with 1.3% SLS and 1.8% procaine |
| 5 | base formulation without procaine, with 1.6% tetracaine and SLS |
| 6 | base formulation without procaine, with 1.6% tetracaine, interferon (Schering Plough, 200,000 units) and SLS. |

The base formulation is as defined for the preferred embodiment of the composition for enhancing heating of viral lesions, but without SLS or anesthetic. Acyclovir (ACV) was used as a positive control (i.e., having anti-viral activity). Placebo (PBS) treated animals were compared with an untreated control animal. 2A was compared with the untreated animals and placebo-treated animals. ACV groups were compared to the placebo-treated group. All others were compared to 2A.

Results

For primary irritation determination, groups of three guinea pigs were treated with each of the samples or controls. No visible signs of any skin irritation or genital toxicity were observed. The animals remained healthy and normal in appearance throughout the study.

Effect on viral replication

After HSV-2 inoculation, viral replication in the vaginal tract reaches a peak on days 3 to 5, then declines gradually with most animals having cleared the virus by day 10. Only 5% ACV given 6 hr after viral inoculation significantly reduced the virus titer-day area under the curve (AUC) or the mean peak virus liter (p-values of 0.05 and <0.01, respectively). Evaluation of topical anti-viral therapy on vaginal virus titers is summarized in Table 1. All other formulations failed to alter vaginal viral replication, regardless of when therapy was initiated.

Effect on Lesion Development

Three to four days after HSV-2 inoculation, vesicular lesions begin to appear on the external genital skin. Lesions progressed to an ulcerative stage by days 7 to 8 and gradually healed by days 15 to 21. Animals treated with the PBS placebo at +6 hr had a significantly increased lesion score-day AUC value when compared to the untreated control group (p-value of <0.05). The vehicle control for the formulations (2A) given at 6 hr had a significantly lower lesion score-day AUC value when compared to the untreated control group (p-value of <0.05). The vehicle control for the formulations (2A) given at +6 hr had a significantly lower lesion score-day AUC when compared to the +6 hr placebo and the untreated control groups (p-value of <0.05 and 0.001 respectively). However, 2A initiated 48 hr post-inoculation resulted in a significantly greater lesion score-day AUC when compared to both the +48 hr placebo and untreated control groups (p-values of <0.01 and 0.001 respectively).

Therapy with 1A, 5, 6 or 5% ACV initiated 6 hr following HSV-2 inoculation significantly decreased lesion development (p-values of <0.05 or less). ACV 5% also reduced the mean peak lesion score (p-value of <0.001). Therapy with these formulations at +48 hr failed to inhibit lesion development. Increased lesion score-day AUC's and mean peak scores were seen with 1A and 5 (p-values of 0.06 or less).

It is important to note that the placebo showed a lesion score of 42.6. Samples 1A, 3, 5, and 6, all containing 1.3% SLS, had scores of 17.2, 31.7, 19.8, and 17.4, respectively, while samples 2A and 3A, not containing SLS, had scores of 27.8 and 21.0, respectively. Samples 3 and 3A had atypical scores, believed to be due to errors in formulation or testing. However, it is evident that the presence of SLS in the formulation reduces the severity of the lesion course in this model.

TABLE 1

EVALUATION OF TOPICAL ANTI-VIRAL THERAPY ON INFECTION RATES AND VAGINAL VIRUS TITERS DURING A PRIMARY GENITAL HSV-2 INFECTION OF GUINEA PIGS

| Treatment[a] | | # Virus Positive/ # Inoculated | Virus Titer-Day Area Under Curve | p-Value | Mean Peak Virus Titer | p-Value |
|---|---|---|---|---|---|---|
| Control | | 10/10 | 23.4 | — | 4.2 | — |
| Placebo (PBS) | +6h | 10/10 | 23.9 | NS[b] | 4.4 | NS |
| 2A | +6h | 10/10 | 22.6 | NS | 3.7 | NS |
| 1A | +6h | 10/10 | 22.1 | NS | 3.6 | NS |
| 3A | +6h | 10/10 | 21.7 | NS | 3.6 | NS |
| 3 | +6h | 10/10 | 24.0 | NS | 3.5 | NS |
| 5 | +6h | 10/10 | 22.1 | NS | 3.6 | NS |
| 6 | +6h | 9/10 | 20.5 | NS | 3.2 | NS |
| ACV 5% | +6h | 10/10 | 14.8 | 0.05 | 2.9 | <0.01 |
| Placebo (PBS) | +48h | 10/10 | 23.0 | NS | 4.0 | NS |
| 2A | +48h | 10/10 | 25.8 | NS | 4.1 | NS |
| 1A | +48h | 10/10 | 26.3 | NS | 4.3 | NS |
| 3A | +48h | 10/10 | 26.3 | NS | 4.3 | NS |
| 3 | +48h | 10/10 | 25.3 | NS | 4.1 | NS |
| 5 | +48h | 10/10 | 27.3 | NS | 4.0 | NS |
| 6 | +48h | 10/10 | 26.6 | NS | 4.3 | NS |

TABLE 1-continued EVALUATION OF TOPICAL ANTI-VIRAL THERAPY ON INFECTION RATES AND VAGINAL VIRUS TITERS DURING A PRIMARY GENITAL HSV-2 INFECTION OF GUINEA PIGS

| Treatment[a] | | # Virus Positive/ # Inoculated | Virus Titer-Day Area Under Curve | p-Value | Mean Peak Virus Titer | p-Value |
|---|---|---|---|---|---|---|
| ACV 5% | +48h | 10/10 | 16.3 | NS | 4.2 | NS |

[a]Treatment was initiated at the times indicated and continued three times daily for seven days both topically and intravaginally.
[b]NS = Not statistically significant when compared to the untreated control or appropriate placebo-treated group. The placebo-treated animals were compared to the untreated control. 2A was compared to the placebo and the untreated control. ACV groups were compared to the placebo-treated group. All others were compared to 2A.

TABLE 2

EVALUATION OF TOPICAL ANTI-VIRAL THERAPY ON LESION DEVELOPMENT DURING A PRIMARY GENITAL HSV-2 INFECTION OF GUINEA PIGS

| Treatment[a] | | Lesion Score-Day Area Under Curve | p-Value | Mean Peak Score | p-Value |
|---|---|---|---|---|---|
| Control | | 35.8 | — | 3.1 | — |
| Placebo (PBS) | +6h | 42.6 | <0.05 ↑ | 3.4 | NS[b] |
| 2A | +6h | 27.8 | <0.05[c] ↓ | 2.8 | NS |
| 1A | +6h | 17.2 | <0.01 ↓ | 2.0 | NS |
| 3A | +6h | 21.0 | NS | 2.8 | NS |
| 3 | +6h | 31.7 | NS | 3.2 | NS |
| 5 | +6h | 19.8 | <0.05 ↓ | 2.5 | NS |
| 6 | +6h | 17.4 | <0.01 ↓ | 2.3 | NS |
| ACV 5% | +6h | 4.9 | <0.001 ↓ | 0.8 | <0.001 ↓ |
| Placebo (PBS) | +48h | 39.2 | NS | 3.1 | NS |
| 2A | +48h | 51.2 | <0.01[c] ↑ | 3.8 | NS[d] |
| 1A | +48h | 59.9 | <0.01 ↑ | 4.3 | <0.05 ↑ |
| 3A | +48h | 56.2 | NS | 4.0 | NS |
| 3 | +48h | 46.8 | NS | 3.7 | NS |
| 5 | +48h | 56.4 | 0.06 ↑ | 4.2 | <0.05 ↑ |
| 6 | +48h | 49.7 | NS | 3.9 | NS |
| ACV 5% | +48h | 41.7 | 0.07 ↑ | 3.7 | NS |

[a]Treatment was initiated at the times indicated and continued three times daily for seven days both topically and intravaginally.
[b]NS = Not statistically significant when compared to the untreated control or appropriate placebo-treated group. The placebo-treated animals were compared to the untreated control. 2A was compared to the placebo and the untreated control. ACV groups were compared to the placebo-treated group. All others were compared to 2A.
[c]p-value was also 0.001 when compared to the untreated control.
[d]p-value was also 0.05 when compared to the untreated control.

EXAMPLE 3

Additional evaluation of the in vivo efficacy of selected components of the composition on a primary genital herpes simplex virus type 2 infection of guinea pigs.

This example sets forth the results of additional studies to establish the efficacy of the compounds in the guinea pig model.

The sodium lauryl sulfate (SLS) and tetracaine preparations tested were purchased from Sigma Chemical Co., St. Louis, Mo. Preparations were dissolved and delivered in phosphate buffered saline (PBS) which was also the placebo vehicle control. The concentrations of each compound utilized alone and in combination were 2%, 1%, and 0.2%.

Virus and Viral Inoculation

The MS strain of HSV-2 was utilized for the animal inoculation. Female Hartley strain guinea pigs (Charles River Breeding Laboratories, Raleigh, N.C.) weighing 250–300 g were inoculated with $2.0 \times 10^5$ plaque forming units of HSV-2 one hours after being swabbed for the removal of vaginal secretions.

Treatment of Guinea Pigs

Groups of 10 guinea pigs were treated both on the external genital skin and intravaginally (0.1 ml each route for a total of 0.2 ml per treatment) for each preparation. Treatments were four times daily (approximately every 6 hours) for 14 days beginning 24 hours post-viral inoculation. Groups of 3 uninfected animals were treated as previously stated with selected preparations to assess toxicity and skin irritation.

Sample Collection and Virus Assays

To determine the effect of treatment on vaginal viral replication, swabs of vaginal secretions were obtained on days 1, 3, 5, 7 and 10 after HSV inoculation, placed in a tube containing 2.0 ml of media and frozen at −70° C. until titrated for HSV-2. When all samples were collected, they were thawed, vortexed, diluted serially and HSV-2 titers were determined using rabbit kidney cells in a microtiter CPE assay.

Evaluation of Efficacy

To determine the effect of therapy on the development and spread of external genital lesions, lesion severity was scored on a 0–5+ scale through the primary infection (21 days). Lesion score-day areas and virus titer-day areas under the curve, and peak lesion scores and peak virus liters between untreated and placebo-treated or drug-treated and placebo-treated animals were compared using the Mann-Whitney U rank sum test. A p-value of 0.05 or less was considered significant.

Effect of Treatment with SLS, Tetracaine or Combinations of SLS plus Tetracaine on Uninfected Guinea Pigs No sign of local skin irritation from any of the formulations was observed. Throughout the treatment period, the genital skin remained normal in appearance, and no redness or swelling was observed. Beginning on day 7 and for the duration of the treatment, there were periodic episodes of an anesthesia-like effect observed in animals receiving 2% tetracaine, and some animals went to sleep. This effect was exhibited approximately 5 minutes after treatment was given and lasted about 20 minutes. It was not always the same animals and not all animals were affected. Some animals went to sleep on several occasions, some times on the same day and some times skipping several treatments. There seemed to be no long term adverse affects following these incidents.

Effect of Treatment with SLS and/or Tetracaine on Vaginal Virus Titers

Viral replication in the vaginal tract after HSV-2 inoculation reaches a peak on days 3–5 and then declines with most animals having cleared the virus by day 10. The effects of administration of the SLS and/or tetracaine preparations on vaginal virus titers are summarized in Table 3. This experiment was designed to show whether or not viral liter reduction is enhanced by the combination of SLS and tetracaine compared to the effects of the individual components. The combinations of SLS and tetracaine at 2% and 1% levels provided significant reductions in viral titer over the individual components at these levels. This effect was not apparent at the 0.2% concentration level. It is interesting to note that SLS generally is more effective than tetracaine in reducing viral titer compared to the placebo.

TABLE 3

EFFECT OF TREATMENT WITH SODIUM LAURYL SULFATE AND/OR TETRACAINE ON VAGINAL VIRUS TITERS OF GUINEA PIGS INOCULATED INTRAVAGINALLY WITH HSV-2

| Treatment[a] | # Virus Positive/ # Inoculated | Virus Titer-Day Area Under Curve | p-Value | Mean Peak Virus Titer | p-Value |
|---|---|---|---|---|---|
| Placebo-PBS | 10/10 | 28.4 | — | 4.6 | — |
| SLS-2% | 10/10 | 19.6 | NS[b] | 3.9 | <0.05 |
| SLS-1% | 7/10 | 18.5 | 0.05 | 3.1 | <0.05 |
| SLS-0.2% | 7/10 | 13.8 | <0.01 | 3.0 | NS |
| Tetracaine-2% | 9/10 | 26.1 | NS | 4.0 | NS |
| Tetracaine-1% | 10/10 | 29.6 | NS | 5.0 | NS |
| Tetracaine-0.2% | 8/10 | 17.5 | NS | 3.6 | NS |
| Tetracaine-2% + SLS-2% | 7/10 | 15.6 | <0.05 | 3.0 | NS |
| Tetracaine-1% + SLS-1% | 7/10 | 13.8 | 0.01 | 3.0 | 0.01 |
| Tetracaine-0.2% + SLS-0.2% | 7/10 | 18.3 | <0.05 | 3.0 | NS |
| Tetracaine-2% + SLS-1% | 7/10 | 14.8 | <0.05 | 3.2 | NS |
| Tetracaine-2% SLS-1% cream | 10/10 | 21.8 | NS | 3.9 | NS |

[a]Topical and i.vag. treatment was initiated 24 hours after viral inoculation and was continued four times daily for 14 days.
[b]NS = Not statistically significant when compared to the placebo-treated group.

TABLE 4

EFFECT OF TREATMENT WITH SODIUM LAURYL SULFATE AND/OR TETRACAINE ON EXTERNAL LESION DEVELOPMENT IN A GENITAL HSV-2 INFECTION OF GUINEA PIGS

| Treatment[a] | Lesion Score-Day Area Under Curve | p-Value | Mean Peak Lesion Score | pValue |
|---|---|---|---|---|
| Placebo-PBS | 24.1 | — | 2.5 | — |
| SLS-2% | 23.3 | NSb | 2.5 | NS |
| SLS-1% | 17.9 | NS | 2.7 | NS |
| SLS-0.2% | 30.7 | <0.05 | 2.7 | NS |
| Tetracaine-2% | 18.5 | NS | 3.1 | NS |
| Tetracaine-1% | 32.3 | NS | 3.3 | NS |
| Tetracaine-0.2% | 15.5 | 0.01 | 1.5 | NS |
| Tetracaine-2% + SLS-2% | 24.6 | NS | 2.8.5 | NS |
| Tetracaine-1% + SLS-1% | 24.3 | NS | 2.6 | NS |
| Tetracaine-0.2% + SLS-0.2% | 25.4 | NS | 2.4 | NS |
| Tetracaine-2% + SLS-1% | 24.1 | NS | 2.8 | NS |
| Tetracaine-2% + SLS-1% cream | 25.0 | NS | 2.9 | NS |

[a]Topical and i.vag. treatment was initiated 24 hours post-viral inoculation and was continued four times daily for 14 days.
[b]NS = Not statistically significant when compared to the placebo-treated group.

Effect of Treatment with SLS, Tetracaine, or Combinations on Lesion Development

Four days after viral inoculation, vesicular lesions begin to appear on the external genital skin. Lesions progress to an ulcerative stage by days 7-8 and gradually heal by days 15-21. The effect of topical treatment with the SLS, tetracaine or combinations of the two on lesion severity is shown in TABLE 4. Mean peak lesion scores were not significantly reduced for any preparation in this study. No other differences on lesion development were observed in this study. This result is explained by a deviation imparted to the standard protocol. Subjects were treated for fourteen rather than seven days. This extended treatment caused the lesions to remain moist (rather than drying out normally) and so healing was impeded. The moist condition of the lesions did not affect the viral titer scores.

EXAMPLE 4

Demonstration of in vivo efficacy in enhancing healing of HSV lesions in humans.

Case report data for six patients was obtained in an open trial using samples containing SLS and procaine. It was shown that the average number of days to healing was reduced to six from a historical mean of ten in the same patients. Furthermore, the course of the disease seemed to be altered favorably. The stages of infection are defined as follows: erythema (Ery); papule (Pap); vesicle (Ves); edema (Ede); and scab (Sea).

Table 5 provides the results of a clinical study in which the cream was applied topically four times daily to a recurring (not primary) lesion:

TABLE 5
Clinical Study Results

| Patient | Average Duration of Episode (Historical) Days | Infection Type | Ery | Pap | Ves | Ede | Sca | Episode Duration (days) |
|---|---|---|---|---|---|---|---|---|
| 1 | 10 | genital | 4 | 0 | 0 | 0 | 0 | 5 |
| 2 | 12 | genital | 5 | 2 | 2 | 2 | 1 | 6 |
| 3 | 10 | labial | 5 | 2 | 0 | 0 | 0 | 5 |
| 4 | 10 | genital | 4 | 3 | 0 | 0 | 0 | 4 |
| 5 | 14 | genital | 6 | 0 | 0 | 0 | 0 | 7 |
| 6 | 6 | genital | 8 | 0 | 2 | 4 | 3 | 8 |
| Average | 10.3 days | | | | | | | Average 5.8 days |

It is important to note that four of the six patients never progressed beyond the papule state and that the average days to healing was reduced by 44%, compared to historical controls which had been on systemic Acyclovir. Lesion-associated pain was reduced or eliminated in all cases.

EXAMPLE 5
Double blinded placebo controlled studies in human subjects suffering from herpes labialis In order to confirm the efficacy of the composition, additional larger scale studies were conducted in human patients. The studies were designed to assess the relative effectiveness and safety of compositions of the invention versus placebo in the treatment of herpes labialis in immunocompetent adults. The composition tested in these studies was designated VT-33 and contained 1.8% tetracaine hydrochloride and 1% sodium lauryl sulfate.

The study was randomized, double-blind, and placebo controlled. Eligible patients were at least eighteen years of age and had prodromal symptomatology or lesions of recurring herpes labialis. Patients in which lesions had been present for more than 48 hours (two days) prior to the initiation of study medication were not eligible for enrollment. Written informed patient consent was obtained.

After enrollment, the medication was self-administered every 2 waking hours, until the lesions healed (scab loss), but for no more than 12 days. A medical history, lesion examination, herpes simplex virus culture of the lesion, blood chemistries, complete blood count and urinalysis were performed on the day of enrollment prior to initiation of the study medication. Subjects were monitored for at least one visit during their treatment and during a final visit after their lesions had healed.

Seventy-two patients were enrolled from four study centers. The patients included in the study were male or female immunocompetent patients at least eighteen years of age with a history of recurring herpes labialis and prodromal symptomatology or clinical signs of herpes labialis in which the lesion had been present for less than 48 hours prior to the initiation of the study. Women of child bearing potential were enrolled provided that they were not pregnant at entry and would not become pregnant during the course of treatment.

The following patients were excluded from the study: (1) patients who could not be evaluated until after lesions had healed, i.e., patients who did not return for the final visit and complete their self-evaluation forms; (2) those less than eighteen years of age; (3) those with a history of immediate hypersensitivity to tetracaine hydrochloride; (4) pregnant or lactating females; (5) immunosuppressed individuals, such as patients with immunodeficiency diseases (or those at high risk for developing immunodeficiency disease), malignancies involving the immune system, or patients receiving immunosuppressant therapy (including cyclosporin, AZT, OKT-3, corticosteroids, alkylating agents and or antimetabolites) within four months prior to presentation or radiation therapy within six months prior to presentation) or patients likely to receive immunosuppressive or radiation therapy during the period of the study drug administration and or during the follow up period; (6) those who had been treated by any route (i.e., oral, topical, parenteral) with any anti-herpes or anti-viral agent within one month prior to or at the time of evaluation for enrollment; (7) those who had been treated with any investigational drug within one month of evaluation for enrollment; (8) those with bacterial superinfection of the herpes simplex lesion at the time of evaluation for enrollment; (9) those whose herpes lesion had been present for more than forty eight hours (2 days) prior to initiation of study; (10) patients with an inability to tolerate the medication; and (11) patients with any condition which, in the opinion of the investigator, would render the subject unfit for the study.

Objective Evaluations

Several objective criteria were used to asses treatment efficacy. Results of these evaluations are set forth below.

Viral Cultures

Sixty-one of the 72 subjects (84.7%) tested positive for herpes simplex virus by viral culture at enrollment.

Time to Scab Formation and Healing (Scab Loss)

Table 6 gives the results of the major objective evaluation parameters of the protocol used for the experiments: time to scab formation and time to healing. There was no difference in the time to scab formation between the placebo and compound VT-33. However, there was a statistically significant difference in the healing time in subjects treated with VT-33 and in subjects treated with the placebo. Subjects treated with VT-33 healed on the average of 5.1 days, and those treated with placebo took longer to heal, on the average of 7.2 days ($p=0.0002$). This is a 29.2% reduction in healing time and indicates that VT-33 is effective in treating recurrent herpes labialis.

TABLE 6
TIME TO SCAB FORMATION AND TIME TO HEAL OF COMPOUND VT-33 VS. PLACEBO IN 72 SUBJECTS (DAYS)

|  | PLACEBO | VT-33 | |
|---|---|---|---|
|  | Mean ± SD (n) | Mean ± SD (n) | p-Value |
| TIME TO SCAB FORMATION | 2.4 ± 0.27 (34) | 2.3 ± 0.26 (32) | 0.4279 |
| TIME TO HEAL | 7.2 ± 0.36 (33) | 5.1 ± 0.35 (33) | 0.0002 |

Figure 1:
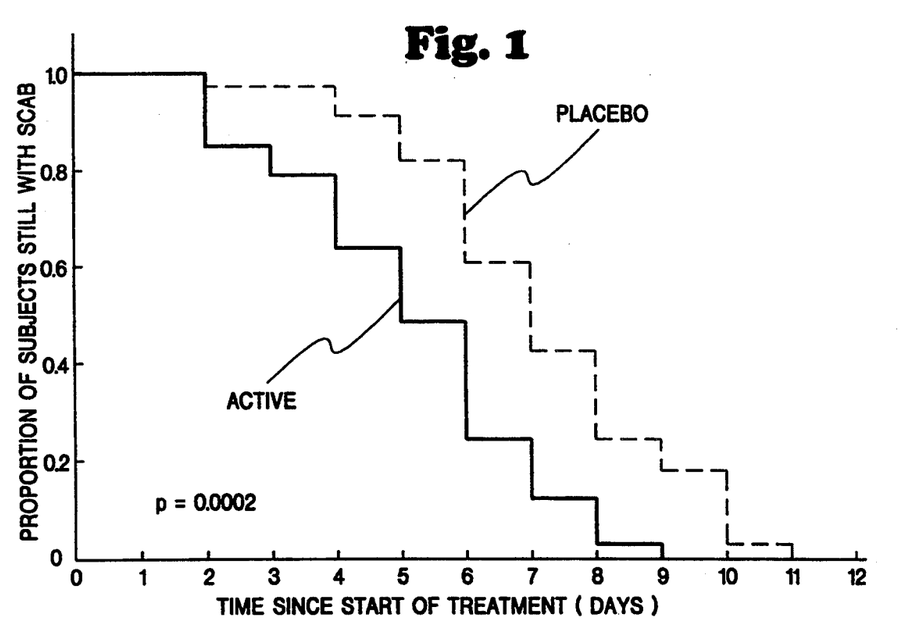
FIG. 1 is a Kaplan-Meier analysis comparing the times to healing of heated versus control lesions.
Figure 2:
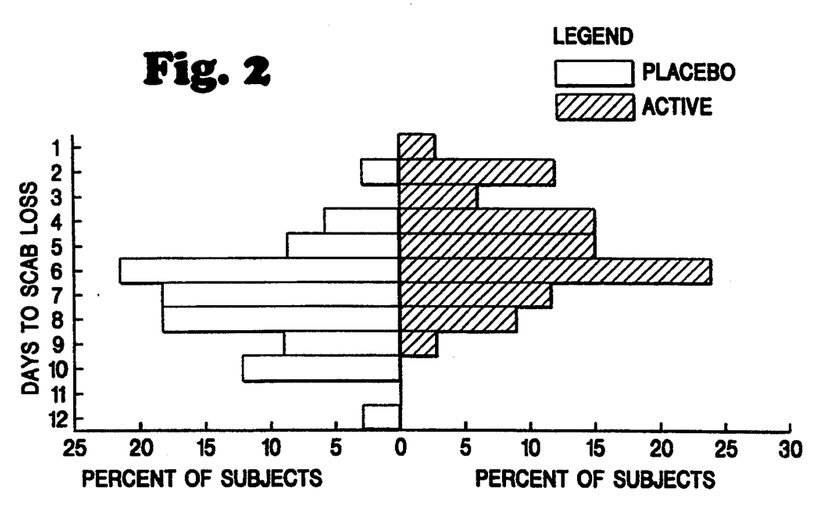
FIG. 2 is a plot the percentage of subjects who healed on a daily basis.

FIG. 1 is a Kaplan-Meir analysis of the distribution of the times to healing and graphically shows the difference between the placebo and VT-33 relative to the proportion of subjects still with scab over the period of treatment. Clearly, VT-33 treatment shifts the healing of the lesions to shorter times. Another graphic representation of this same data is shown in FIG. 2, a plot of the percentage of subjects who healed on a daily basis. As seen the VT-33 curve is again shifted to shorter healing times as compared to the placebo curve.

Subjective Evaluations

In addition to the objective observations shown above, subjective patient impressions were monitored during the study. Summary data on self-rating scales for pain relief by day on-study are shown in Table 7. Lower scores indicate less intense pain perceived by the subject. There were no statistically significant differences between treatment groups on self-ratings on pain intensity.

TABLE 7
Means, Standard Errors, and Sample Sizes of Individual Rating Scales for Relief of Pain by Day and Treatment Group.

| Day On-Study | Placebo Mean ± S.E. (n) | Active Mean ± S.E. (n) |
|---|---|---|
| 1 | 3.8 ± 0.32 (32) | 3.7 ± 0.33 (35) |
| 2 | 3.2 ± 0.34 (33) | 3.0 ± 0.28 (35) |
| 3 | 2.8 ± 0.35 (33) | 2.5 ± 0.29 (35) |
| 4 | 2.2 ± 0.31 (33) | 1.9 ± 0.21 (35) |
| 5 | 1.8 ± 0.32 (32) | 1.6 ± 0.19 (33) |
| 6 | 1.8 t 0.25 (31) | 1.5 ± 0.14 (34) |
| 7 | 1.5 ± 0.16 (29) | 1.3 ± 0.10 (30) |

Summary data on self-rating scales for intensity of itching by day on-study are shown in Table 8. Lower scores indicate less intense itching. There was statistically significantly lower self-rating of itching reported by the Active group on days two and three of the study.

TABLE 8
Means, Standard Errors, and Sample Sizes of Individual Rating Scales for Relief of Itching by Day and Treatment Group.

| Day On-Study | Placebo Mean ± S.E. (n) | Active Mean ± S.E. (n) |
|---|---|---|
| 1 | 3.1 ± 0.36 (32) | 3.7 ± 0.47 (35) |
| 2[a,b] | 3.1 ± 0.42 (28) | 2.3 ± 0.30 (34) |
| 3[a,b] | 2.7 ± 0.36 (31) | 2.0 ± 0.26 (35) |
| 4 | 2.0 ± 0.26 (29) | 1.5 ± 0.16 (32) |
| 5 | 1.6 ± 0.22 (29) | 1.3 ± 0.12 (33) |
| 6 | 1.4 ± 0.18 (29) | 1.2 ± 0.07 (35) |
| 7 | 1.3 ± 0.14 (25) | 1.1 ± 0.06 (30) |

[a]Student t-test, p < 0.05, one-tailed.
[b]Mann-Whitney U-test, p < 0.05, one-tailed.

Summary data of self-rating scales for perceived benefit by day on-study are shown in Table 9. Higher scores indicate a larger perceived benefit. There were no statistically significant differences between treatment groups on self-ratings of perceived benefit at the beginning of the study. However, as the study progressed the perceived benefit was rated significantly higher by the Active group as compared to the Placebo group on days three through seven.

TABLE 9
Means, Standard Errors, and Sample Sizes of Individual Rating Scales for Perceived Benefit by Day and Treatment Group.

| Day On-Study | Placebo Mean ± S.E. (n) | Active Mean ± S.E. (n) |
|---|---|---|
| 1 | 3.1 ± 0.66 (18) | 3.1 ± 0.60 (20) |
| 2 | 4.5 ± 0.56 (31) | 5.6 ± 0.47 (33) |
| 3[a,b] | 4.9 ± 0.55 (32) | 6.5 ± 0.40 (31) |
| 4[a,b] | 5.4 ± 0.58 (31) | 7.0 ± 0.44 (31) |
| 5[a] | 5.9 ± 0.59 (32) | 7.1 ± 0.44 (31) |
| 6[a,b] | 5.4 ± 0.59 (32) | 7.2 ± 0.45 (33) |
| 7[a,b] | 5.4 ± 0.61 (30) | 7.6 ± 0.51 (29) |

[a]Student t-test, p < 0.05, one-tailed.
[b]Mann-Whitney U-test, p < 0.05, one-tailed.

Table 10 shows the subject's self-evaluation of the overall benefit of treatment, where benefit was ranked on an index score of 1–10 (1=no benefit; 10=very effective treatment) at the end of treatment. Subjects who were treated with VT-33 ranked the overall benefit of their treatment at an index significantly higher than of the placebo-treated group (7.3 vs. 5.9), which indicates that the VT-33 treated group had a better subjective opinion of the medication than did the placebo-treated subjects.

TABLE 10
SUBJECT SELF-EVALUATION OF BENEFIT OF TREATMENT
VT-33 VS. PLACEBO
TREATMENT BENEFIT INDEX (n)

| PLACEBO | 5.9 ± .60 (34) |
|---|---|
| VT-33 | 7.3 ± .48 (37) | p = .0359
INDEX
1 = No Benefit At All
10 = Very Effective Treatment

Investigator's Evaluation

The clinical investigators were also asked to evaluate the study medications for their relative effects on the following subjective parameters: (1) relief from pain; (2) relief from itching; (3) ability to heal; and (4) overall clinical effectiveness. Ranking was on an index scale of 1–10 (1=very unfavorable; 10=very favorable). As shown in Table 11, there was no statistical difference between the investigators ranking in the above categories. One category, relief from itching, approached statistical significance.

TABLE 11
INVESTIGATOR'S EVALUATION OF RELIEF FROM PAIN, RELIEF FROM ITCHING, OVERALL HEALING EFFECT, AND GENERAL CLINICAL BENEFIT (OF COMPOUND VT-33 VERSUS PLACEBO)

|  | PLACEBO (n) | VT-33 (n) | p-VALUE |
|---|---|---|---|
| RELIEF FROM PAIN | 6.9 ± 0.55 (33) | 7.8 ± 0.45 | .0921 |
| RELIEF FROM ITCHING | 6.7 ± 0.57 (32) | 7.9 ± 0.44 | .0533 |
| ABILITY TO HEAL | 6.6 ± 0.63 (33) | 6.9 ± 0.53 | .3526 |
| OVERALL CLINICAL | 6.6 ± 0.60 (33) | 7.3 ± 0.48 | .1917 |

TABLE 11-continued

INVESTIGATOR'S EVALUATION OF RELIEF FROM PAIN, RELIEF FROM ITCHING, OVERALL HEALING EFFECT, AND GENERAL CLINICAL BENEFIT (OF COMPOUND VT-33 VERSUS PLACEBO)

| | PLACEBO (n) | VT-33 (n) | p-VALUE |
|---|---|---|---|
| EFFECTIVENESS | | | |

INDEX
1 = Very Unfavorable
10 = Very Favorable

The results set forth above establish that compounds of the invention, as exemplified by compound VT-33, effectively shortened the healing time of recurrent herpes labialis lesions by nearly 30% in a controlled clinical setting. Because of the design of this study, patients began treatment as late as 48 hours after the appearance of their lesions. Therefore, it is possible that self-initiated therapy at the beginning of lesion appearance or at prodrome would result in a further shortening of healing time. Additionally, the patients' impression of the benefit of the compound was significantly higher than that for the placebo. The more conservative view of the investigators is contradicted by the objective indications and patients' impressions, and therefore, may not represent an accurate assessment, particularly since the clinicians were asked to evaluate parameters, such as pain and itching, that they did not themselves experience.

Modifications and variations of the composition and method of the present invention will be obvious to those skilled in the art. Such modifications and variations are intended to come within the scope of the appended claims.

What is claimed is:

1. A method for treatment of a herpetic lesion comprising topically administering to said lesion a composition comprising the combination of:
    (a) tetracaine, in a concentration of from about 1% to 2% by weight; and
    (b) sodium lauryl sulfate in a concentration of from about 0.5% to about 5.0% by weight, and
    wherein said combination is administered in a pharmaceutically acceptable carrier for topical administration.

2. The method of claim 1 wherein said composition comprises from 1% to 2% tetracaine and 1% sodium lauryl sulfate.

3. The method of claim 1 wherein said composition is applied to the lesion at least once every twelve hours.

4. The method of claim 1 wherein said treatment reduces viral titer in said lesion and thereby lowers infectivity of said lesion.

* * * * *